United States Patent [19]

Cavalla et al.

[11] 4,046,767

[45] Sept. 6, 1977

[54] PIPERIDINO COMPOUNDS

[75] Inventors: John Frederick Cavalla, Isleworth; John Leheup Archibald, Windsor, both of England

[73] Assignee: John Wyeth & Brother Limited, Maidenhead, England

[21] Appl. No.: 697,081

[22] Filed: June 16, 1976

Related U.S. Application Data

[60] Division of Ser. No. 564,508, April 2, 1975, which is a continuation-in-part of Ser. No. 323,684, Jan. 15, 1973, which is a continuation-in-part of Ser. No. 175,345, Aug. 26, 1971, abandoned.

[30] Foreign Application Priority Data

Sept. 3, 1970  United Kingdom ............... 42090/70
July 22, 1971  United Kingdom ............... 34376/71

[51] Int. Cl.² ............................................ C07B 211/36
[52] U.S. Cl. ........................... 260/293.77; 260/293.58
[58] Field of Search .......................260/293.58; 293.77

OTHER PUBLICATIONS

Harper, et al., Jour. Med. Chem., vol. 7 (1964) p. 729-32.

[56] References Cited

FOREIGN PATENT DOCUMENTS 1,345,872  2/1974  United Kingdom ............ 260/293.77

OTHER PUBLICATIONS 260 293.58;293.77

*Primary Examiner*—Norma S. Milestone
*Attorney, Agent, or Firm*—Arthur E. Wilfond

[57] ABSTRACT

Novel piperidine compounds and their use in treatment of disorders and diseases of the cardiovascular system and/or in the treatment of superficial and deep allergic phenomena is described. These compounds are piperidine compounds linked by the nitrogen atom to cycloalkyl or a substituted or unsubstituted phenyl radical through the intermediary of a lower-alkylene radical. The piperidine ring is further substituted by an acylamino residue.

13 Claims, No Drawings

PIPERIDINO COMPOUNDS

This application is a divisional of our copending application Ser. No. 564,508 filed Apr. 2, 1975 which is a continuation-in-part of our copending application Ser. No. 323,684 filed Jan. 15, 1973 now abandoned, and entitled "Heterocyclic Compounds" now abandoned, which is a continuation-in-part of our application Ser. No. 175,345 filed Aug. 26, 1971 entitled "Pharmaceutical Compositions" and now abandoned.

This invention relates to novel piperidino compounds and to the use of these compounds in a method of treating disorders and diseases of the cardiovascular system, particularly hypertension, and/or deep superficial allergic phenomena in mammals.

The invention provides a compound of formula is

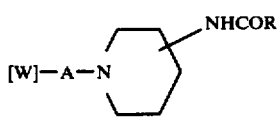
Ia wherein [W] represents cyclohexyl, monohalophenyl, dihalophenyl, lower alkoxyphenyl, dilower alkoxyphenyl, trilower alkoxyphenyl, trilower alkoxyphenyl, di(-loweralkyl)phenyl, methylenedioxyphenyl, lower alkanoylaminophenyl, nitrophenyl, or aminophenyl, A is lower alkylene of 1 to 6 carbon atoms, and R represents phenyl or a pharmaceutically acceptable acid addition salt thereof.

It is to be understood that the term "alkylene" used herein includes both straight and branched chain radicals, the term "lower" means the radical concerned contains 1 to 6 carbon atoms, preferably 1 to 4 carbon atoms.

The compounds of formula (Ia) and the pharmaceutically acceptable acid addition salts thereof exhibit pharmacological activity particularly hypotensive and/or anti-hypertensive activity or other action on the cardiovascular system (such as peripheral vasodilation and/or anti-anginal and/or anti-arrhythmic activity), anti-histamine activity such as activity against superficial and deep allergic phenomena, for example, Urticaria, Pruritus, Allergic Rhinitis, Anaphylactic shock and Asthma, and sometimes central nervous system activity (such as sedative or anti-convulsant activities) and anti-inflammatory activity when tested on warm-blooded animals. The compounds of formula Ia which have been prepared and tested have been found to possess hypotensive activity.

However, certain compounds are similar in structure to known compounds of formula Ia wherein W is an unsubstituted phenyl radical and A is —CH₂— or —CH₂CH₂—. The known compounds were described by Harper and Chignell, J. Med. Chem., 1964, 7, 729-732. These known compounds were employed by Harper & Chignell as chemical intermediates for other compounds which were tested for CNS and analgesic activity.

A preferred group of compounds of the invention comprises those of formula Ia wherein W is as defined above and A is lower alkylene of 2-4 carbon atoms. Especially preferred compounds of formula Ia are those where W is dimethoxyphenyl and o-aminophenyl.

The compounds of formula Ia form part of a larger group of compounds of formula I₂

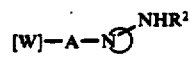

wherein

represents a ring system of formula

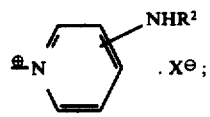
II(a)

II(b)

or

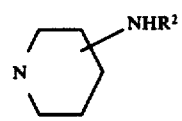
II(c)

wherein W and A are as herein defined and R² is hydrogen or the group COR, where R represents a phenyl radical.

Examples of W are phenyl substituted by one or more groups, selected from halogen (for example fluorine, chlorine or bromine), lower alkoxy (for example methoxy, ethoxy, propoxy or butoxy), nitro, amino, acylamino in particular alkanoylamino [for example acetylamino (acetamido)], and alkylenedioxy (for example methylenedioxy).

The compounds of general formula (I) can be prepared in a number of ways by building up the molecule from suitable starting materials in known manner. Such processes applied to the preparation of the novel compounds of formula (Ia) are included in the scope of the invention.

One method of preparation of compound of general formula (I) in which R² is the —COR group comprises reacting a compound of the general formula

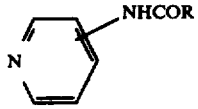
III(a)

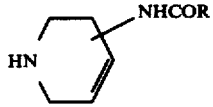
III(b)

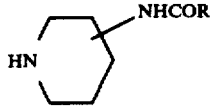
III(c)

with an alkylating or acylating agent of the general formula

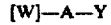
(IV)

where R, W and A have the meanings already defined and Y is a halogen atom or an equivalent replaceable atom or radical, for example an organic sulphonyl radical such as tosyl radical.

The compounds of general formula (IV), are known compounds or can be made following the methods known for preparing compounds of these types. The starting materials of general formulae III(a), III(b) and III(c) can generally be made by acylating a corresponding amino compound of the general formula

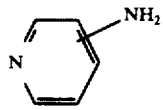

(VIII)

and if necessary reducing the ring system to the corresponding tetrahydropyridine or piperidine ring. The starting material of general formula III(c) is preferably prepared by either (i) forming the oxime of an N-benzyl-4-piperidone, reducing to give the 4-amino compound, acylating the amino group and then hydrogenolysing the benzyl residue, or (ii) treating the pyridine of formula

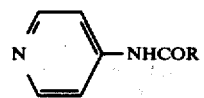

(IX)

with a benzyl halide, for example benzyl chloride to give the quaternary salt, reducing with an alkali metal borohydride to give the corresponding N-benzyl-tetrahydro-pyridine with is further subjected to concomitant de-benzylation and reduction of the 3,4-double bond by catalytic hydrogenation, or (iii) catalytic hydrogenation of compound (IX) in the presence of acetic anhydride to give

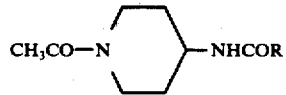

(X)

and then selectively hydrolysing the acetyl group.

A second general method of preparation of compounds of formula (I) in which $R^2$ is the —COR group, comprises reacting a compound of formula (I) in which $R^2$ is a hydrogen atom, with either a reactive derivative of an acid of general formula R.COOH (where R is phenyl). As a reactive derivative of the acid of formula R.COOH used in the process described above, we have found it preferable usually to use a halide (for example the chloride or bromide) or an anhydride. Other examples of reactive derivatives of the acid R.COOH which may be used are the acid azide, mixed anhydrides and active esters. Furthermore, the compounds of formula (I) in which $R^2$ is the —COR group may also be prepared by treating a compound of formula (I) in which $R^2$ is a hydrogen atom with the acid R.COOH in the presence of a known condensing agent (for example, a carbodiimide), or by first activating the amino function (for example, by forming the phosphazo derivative) and then reacting with the acid R.COOH. In connection with the introduction of the —COR group into a compound of formula (I) in which $R^2$ is a hydrogen atom, reference may be made to "Chemistry of the Amino Acids" by Greenstein and Winitz (John Wiley & Sons. Inc., Publishers, 1961) at pages 782–883 and 943–1108.

When it is desired to prepare a compound of general formula (I) wherein $R^2$ is a hydrogen atom, a corresponding compound of formula

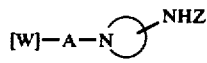

(XII)

(wherein W, has the meaning defined in connection with formula (I),

represents a ring system of formula

XIII(a)

XIII(b)

or

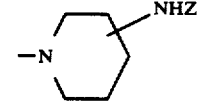

XIII(c)

and Z is a protecting group known in the art for the protection of the amino function and A has the meanings defined immediately above), is subjected to hydrolysis, hydrogenolysis or some other reaction known in the art for the removal of the protecting group Z. As examples of Z, mentioned is made of those wherein Z is the group —COR and R is lower alkyl, lower alkoxy and aryloxy (particularly methyl, ethoxy and phenoxy respectively) or aryl. Other examples of Z are benzyl, p-toluenesulphonyl, phthalyl, trityl, trifluoroacetyl, formyl and benzyl-sulphonyl. Reference may be made to the review of protecting groups in Advances in Organic Chemistry, 3, 191–294 (Interscience Publishers 1963), and also to Chemistry of the Amino Acids by Greenstein and Winitz, Vol. 2, pages 885–924 (John Wiley & Sons, Inc., 1961). The compounds of general formula (XII) can be prepared following the information already given but using the appropriate acylating agent or other reagent to introduce the group Z.

A still further aspect of the invention is the provision of a further process for the preparation of compounds of general formula (I) in which

represents a ring system of formula II(b) or II(c), W has the meanings defined in connection with formula (I), $R^2$ is the group —COR, R has the meanings defined in connection with formula (I) and A is a lower alkylene radical and wherein the process consists of reacting a compound of the general formula

[W]—A—OH     (XVI)

(in which W, and A have the meanings defined immediately above) with a compound of formula III(b) or III(c) (in which $R^2$ has the meaning defined immediately above).

The reaction is preferably carried out in the presence of a catalyst, for example Raney Nickel. An organic solvent, which is inert under the reaction conditions, is usually used for example xylene, toluene or benzene. Preferably the reaction is carried out by heating the reactants under reflux in a water-immiscible organic solvent, for example xylene, and removing the water formed during the reaction by azeotropic distillation. If necessary, reactive substituent groups can be blocked during a reaction and released later.

The reactions outlined above usually are carried out in a solvent which is inert under the reaction conditions. The most suitable solvent system is chosen and varies depending on the particular reactants being employed. If necessary heating the reactants in solution under reflux can be carried out, and if necessary heating under high pressures may also be used.

Once a compound of general formula (I) has been prepared, then if necessary one or more substituents in the molecule may be converted to another substituent each within its own meanings specified in connection with formula (I). If a compound is produced in which

represents the pyridinium ring system of formula II(a), this may be selectively reduced to one of the other ring systems of lower oxidation state. For example, reduction with an alkali metal borohydride gives the tetrahydropyridine ring system of formula II(b). On the other hand, catalytic hydrogenation, for example, in the presence of Raney Nickel or a platinum catalyst, gives rise to the piperidine ring system of formula II(c). Similarly, if a compound of formula (I) is prepared in which

represents the tetrahydropyridine ring system of formula II(b), this may also be reduced to the piperidine ring system of formula II(c).

Compounds of formula (I) may also be prepared from corresponding compounds in which the chain A contains one or more carbonyl functions and then this chain may be selectively reduced. For example, when A is the oxalyl residue —CO.CO—, this may be reduced under conditions such that the ethylene chain —CH$_2$—CH$_2$— results.

When a compound of formula (I) is produced wherein the radical W has one or more methoxy substituents, demethylation to the corresponding hydroxyl compound may be brought about in known manner. Furthermore, if the radical W has a nitro substituent this may be reduced in known manner to the corresponding amino compound which in turn may be further acylated or alkylated.

If necessary, in any of the reactions hereinbefore described, reactive substituent groups may be blocked during a reaction and released at a later stage. As already indicated the novel tetrahydropyridine and piperidine compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

The compounds of formula Ia may be used in pharmaceutical compositions which contain as active ingredients a compound of formula (Ia) as hereinbefore defined, which may be micronised. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this is can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following non-limiting Examples illustrate the invention. Examples 2–4 illustrate the preparation of intermediates useful in preparing compounds to be used in the methods of the invention the remaining examples illustrate the preparation of compounds used in the invention.

EXAMPLE 1

1-[2-(Cyclohexyl)ethyl]-4-benzamidopiperidine

2-Cyclohexylethyl bromide (1.9 g.) in dimethylformamide (10 ml) was added to 4-benzamidopiperidine (2.2 g.), diisopropylamine (4 ml.) and a trace of sodium iodide in dimethylformamide (10 ml.). The mixture was heated at 70° C for 16 hours, cooled, poured into water, and extracted with methylene chloride. The washed and dried extracts were evaporated and the solid residue was recrystallised from ethanol to give the produce (1.25 g.), m.p. 174°–5° C. (Found: C, 76.4; H, 9.5; N, 8.9. $C_{20}H_{30}N_2O$ requires C, 76.4; H, 9.6; N, 8.9%).

The product exhibits good hypotensive activity in standard test procedures.

EXAMPLE 2

1-[2-(3,4-Dimethoxyphenyl)ethyl]-4-acetamidopyridinium iodide 1-(2-Iodoethyl)-3,4-dimethoxybenzene (29.3 g.) and 4-acetamidopyridine (14.0 g.) in absolute ethanol (100 ml.) were refluxed for 2.5 hours. The resulting crystalline material was collected and recrystallised from ethanol to give the title compound (29.1 g.)., m.p. 201°–202° C. (Found: C, 47.9; H, 4.9; N, 6.3; $C_{17}H_{21}IN_2O_3$ requires C, 47.7; H, 4.9; N, 6.5%).

The product is an intermediate for the corresponding piperidine compound.

EXAMPLE 3

1-[2-(3,4-Dimethoxyphenyl)ethyl]-4-acetamidopiperidine

The quaternary salt of Example 2 (50 g.) and W7 Raney nickel (ca. 30 g.) in ethanol (600 ml.) containing triethylamine (13.1 g.) was hydrogenated at 700 p.s.i. and 80° C. for 4 hours. The filtrate, after removal of the catalyst was evaporated to dryness. Trituration of the residue with 2N sodium hydroxide solution caused crystallisation of 30.1 g. of the title compound, m.p. 152°–4° C. (Found: C, 66.4; H, 8.6; N, 9.1. $C_{17}H_{24}N_2O_3$ requires C, 66.6; H, 8.6; N, 9.1%).

The product exhibits depressant activity but is primarily useful as an intermediate for the corresponding 4-amino compound.

EXAMPLE 4

1-[2-(3,4-Dimethoxyphenyl)ethyl]-4-aminopiperidine

The acetamido compound of Example 3 (2.5 g.) in 2N hydrochloric acid (25 ml.) was treated under reflux for 3.5 hours. The cooled solution was basified and extracted with chloroform. Evaporation of the washed and dried extracts gave an oil which was treated with ethanolic hydrogen chloride to provide 1.67 g. of the title compound as its dihydrochloride, m.p. 260°–263° C. (Found: C, 53.4; H, 7.7; N, 8.3. $C_{15}H_{24}N_2O_2.2HCl$ requires C, 53.3; H, 7.8; N, 8.3%).

This compound exhibits hypotensive and depressant activity but is primarily useful as an intermediate for the corresponding 4-benzamido compound.

EXAMPLE 5

1-[2-(3,4-Dimethoxyphenyl)ethyl]-4-benzamidopiperidine

The amine dihydrochloride of Example 4 (2.0 g.) in methylene chloride (100 ml.) was stirred with potassium carbonate (2.76 g.) in water (50 ml.). Benzoyl chloride (1.8 ml.) in methylene chloride (20 ml.) was added slowly dropwise. Stirring was continued for 2 hours. The aqueous layer was separated and extracted with methylene chloride. Evaporation of the washed and dried methylene chloride layers gave an oil which was crystallised from ethanol to provide 1.80 g. of the title compound, m.p. 194°–195° C. (Found: C, 71.7; H, 7.7; N, 7.5. $C_{22}H_{28}N_2O_2$ requires C, 71.7; H, 7.7.; N, 7.6%).

The product exhibits marked hypotensive activity.

EXAMPLE 6

1-[2-(3,4,5-Trimethoxyphenyl)ethyl]-4-benzamidopiperidine

Prepared in exactly the same way as for the compound of Example 1 except that 3,4,5-trimethoxyphenethyl chloride was used in place of cyclohexylethyl bromide. The title compound was obtained as a monohydrate (1.2 g.), m.p. 193°–4° C. (Found: C, 66.7; H, 7.6; N, 6.9. $C_{20}H_{30}N_2O_4.H_2O$ requires C, 66.4; H, 7.5; N, 6.7%).

The product exhibits hypotensive and depressant activity.

EXAMPLE 7

1-[2-(p-Nitrophenyl)ethyl]-4-benzamidopiperidine p-Nitrophenylethyl bromide (1.15 g.) was refluxed for 20 hours in isopropyl alcohol (75 ml.) with 4-benzamidopiperidine (1.032 g.) and anhydrous potassium carbonate (1.037 g.). The mixture was filtered hot, refrigerated and product was filtered off (547 mg.), washed with cold isopropyl alcohol and ether. The filtrate was evaporated to yield more product (1.4 g.). Recrystallisation from a mixture of benzene and petroleum ether (b.p. 40°–60° C) gave the title compound, m.p. 209°–216° C. (Found: C, 68.2; H, 6.7; N, 11.8. $C_{20}H_{23}N_3O_3$ requires C, 68.0; H, 6.6; N, 11.9%).

The product exhibits hypotensive activity and also depressant and anti-tremorine activities.

EXAMPLE 8

1-[2-(p-Aminophenyl)ethyl]-4-benzamidopiperidine

1-[2-(p-Nitrophenyl)ethyl]-4-benzamidopiperidine (3.0 g.) was hydrogenated in absolute alcohol (400 ml.) at 50 p.s.i. and 20° C for 3 hours in the presence of 300 mg. of platinum oxide as catalyst. The catalyst was filtered off and the solution evaporated to give the crude product as a foam. Crystallisation from a mixture of benzene and n-hexane gave the title compound, m.p. 193°-195° C. (Found: C, 74.4; H, 7.9 N, 12.9. $C_{20}H_{25}N_3O$ requires C, 74.3; H, 7.8; N, 13.0%).

The product exhibits hypotensive activity and also depressant activity.

EXAMPLE 9

1-[2-(p-Acetamidophenyl)ethyl]-4-benzamidopiperidine

1-[2-(p-Aminophenyl)ethyl]-4-benzimadopiperidine (2.3 g.) was refluxed for 2 hours with acetic anhydride (22 ml.) in anhydrous pyridine (100 ml.). The solution was refrigerated for 24 hours and a crystalline product was filtered off, which after washing with ether yielded the title compound, m.p. 270°-275° C(dec.). Found: C, 72.6; N, 7.55; N, 11.6. $C_{22}H_{27}N_3O_2$ requires C, 72.3; H, 7.45; N, 11.5%).

The product exhibits hypotensive activity and also depressant and anti-tremorine activities.

EXAMPLE 10

1-[2-(o-Nitrophenyl)ethyl]-4-benzamido-piperidine

A mixture of 2-(o-nitrophenyl)ethyl bromide (1.15 g.), 4-benzamidopiperidine (1.02 g.) and potassium carbonate (1.04 g.) in isopropanol (75 ml.) was stirred and refluxed for 24 hours. The hot mixture was filtered, the filtrate evaporated and the residue crystallised from ethanolic hydrogen chloride and ether to give the title compound as the hydrochloride, (47 mg.), m.p. 236°-241° C. (Found: C, 61.31; H, 6.1; N, 10.6. $C_{20}H_{23}N_3O_3.HCl$ requires C, 61.6; H, 6.2; N, 10.8%).

The product exhibits hypotensive activity.

EXAMPLE 11

1-[2-(o-Aminophenyl)ethyl]-4-benzamidopiperidine

A solution of 1-[2-(o-nitrophenyl)ethyl]-4-benzamidopiperidine (4.25 g.) in absolute ethanol (150 ml.) was added over 50 minutes to stirred stannous chloride (10.82 g.) in concentrated hydrochloric acid (12 ml.). and water (7.5 ml.) at 60°-70° C. After addition, the mixture was stirred at this temperature for 4 hours before cooling and evaporating the ethanol. Continuous extraction into chloroform of the neutralised (with 2N sodium hydroxide solution) aqueous fraction gave the title compound (1.65 g.). The aqueous layer after extraction was made alkaline with 2N sodium hydroxide solution and extracted with more chloroform to give a further batch of the title compound (2.36 g.). The total product was crystallised from ethanolic hydrogen chloride and ether to give the hydrochloride of the title compound (2.75 g.), m.p. 263.8° C. (Found: C, 60.3; H, 7.0; N, 10.5. $C_{20}H_{25}N_3O$. 2HCl requires C, 60.6; H, 6.9; N, 10.60%).

The product exhibits hypotensive and depressant activities.

EXAMPLE 12

1-[2-(3,4-Dichlorophenyl)ethyl]-4-benzamidopiperidine

4-Benzamidopiperidine (204 mg.) and anhydrous potassium carbonate (138 ml.) were intimately ground together and added to 2-(3,4-dichlorophenyl)ethyl bromide (254 mg.). The resulting paste was heated at 100° C for 2 hours to give a hard solid. This was broken up, washed well with water and ether and dried to give the title compound (355 mg.). Recrystallisation from ethanolic hydrogen chloride and ether gave the hydrochloride (237 mg.), m.p. 286.0° C. (Found: C, 58.2; H, 5.8; N, 6.8. $C_{20}H_{22}Cl_2N_2O.HCl$ requires C, 58.05; H, 5.6; N, 6.8%).

The product exhibits good hypotensive activity. It also possesses α-adrenoceptor antagonism, antihistamine and and anti-tremorine activities.

EXAMPLE 13

1-[2-(2,6-Dichlorophenyl)ethyl]-4-benzamidopiperidine 2-(2,6-Dichlorophenyl)ethyl bromide (674 mg.) was reacted with 4-benzamidopiperidine (547 mg.) in the presence of anhydrous potassium carbonate (736 mg.) following the procedure of Example 12 to give the title compound as the hydrochloride (412 mg.) m.p. 285.7° C after crystallisation from ethanolic hydrogen chloride and ether. (Found: C, 58.0; H, 5.6; N, 6.7. $C_{20}22Cl_2N_2O$. HCl requires C, 58.05; H, 5.6; N, 6.8%).

The product exhibits hypotensive activity, also anti-tremorine and depressant activites.

EXAMPLE 14

A.

1-[4-(4-Fluorophenyl)-4-oxobutyl]-4-benzamidopiperidine

4-Benzamidopiperidine (2.0 g.), 4'-chloro-p-fluorobutyrophenone (1.0 g.) and a trace of sodium iodide in dimethylformamide (5 ml.) were maintained at 70° C for 18 hours. On cooling, the solid which separated was collected, suspended in water, and refiltered. Recrystallisation from ethanol-water gave the title compound (0.52 g.), m.p. 161°-2° C. (Found: C, 71.9; H, 6.85; N, 7.5. $C_{22}H_{25}FN_2O_2$ requires C, 71.7; H, 6.8; N, 7.6%).

B.

1-[4-(p-Fluorophenyl)-n-butyl]-4-benzamidopiperidine

Hydrazine hydrate (80%, 60 ml.) was added to 1-[4-(p-fluorophenyl)-4-oxobutyl]-4-benzamidopiperidine (11.08 g.) dissolved in warm ethylene glycol (125 ml.) and the solution was refluxed gently for 60 minutes (135°-140° C). Potassium hydroxide pellets were added (6.0 g.) and excess water and hydrazine were distilled off until the temperature rose to 185° C. Refluxing was continued for 30 minutes at this temperature and the hot solution was poured into cold water (500 ml.). The precipitated product was filtered off and after two crystallisations from ethanolic hydrogen chloride and ether the hydrochloride, hemihydrate of the title compound was obtained (1.85 g.) m.p. 228.3° C. (Found: C, 66.1; H, 7.4; N, 7.4. $C_{22}H_{27}FN_2O$. HCl. $\frac{1}{2}H_2O$ requires C, 66.1; H, 7.3; N, 7.0%).

The product exhibits hypotensive activity and also α-adrenoceptor antagonism and anti-histamine activity.

EXAMPLE 15

1-[2-(3,4-Dimethylphenyl)ethyl]-4-benzamidopiperidine 2-(3,4-Dimethylphenyl)ethyl bromide (4.57 g.) was combined with 4-benzamidopiperidine (4.09 g.) in the presence of anhydrous potassium carbonate (2.76 g.) following the procedure of Example 12 to give the hydrochloride, hydrate of the title compound (3.07 g.), m.p. 276.0° C. (Found: C, 67.9; H, 7.7; N, 7.1. $C_{22}H_{28}N_2O \cdot HCl \cdot H_2O$ requires C, 67.6; H, 8.0; N, 7.2%).

The product exhibits hypotensive activity.

EXAMPLE 16

4-Benzamido-1-(3,4-methylenedioxybenzyl)piperidine 3,4-Methylenedioxybenzyl chloride (5.76 g.), 4-benzamido-piperidine (6.89 g.) and anhydrous potassium carbonate (7.00 g.) were stirred at room temperature for 5 hours in isopropanol (50 ml.). Additional isopropanol (100 ml.) was added and stirring continued for 3 hours. The mixture was then heated to the boiling point and filtered whilst hot. Filtration provided the title compound as the hemi-hydrate (7.94 g.), m.p. 179.5°–180.5° C. A second crop (1.23 g.) was obtained on concentration of the mother liquors. (Found: C, 69.2; H, 6.55; N, 8.2. $C_{20}H_{22}N_2O_3 \cdot \frac{1}{2}H_2O$ requires C, 69.15; H, 6.7; N, 8.1%).

The product exhibited hypotensive activity and also anti-inflammatory activity.

EXAMPLE 17

4-Benazmido-1-[2-(p-chlorophenyl)ethyl]piperidine 2-(p-Chlorophenyl)ethanol p-toluenesulphonate ester (9.8 g.), 4-benzamidopiperidine (6.49 g.) and anhydrous potassium carbonate (8.78 g.) were refluxed in isopropanol (150 ml.) for 12 hours and the mixture filtered hot. On cooling, the filtrate deposited the title compound as colourless crystals, (5.4 g.), m.p. 190°–195° C. (Found: C, 70.3; H, 6.9; N, 8.1. $C_{20}H_{23}ClN_2O$ requires C, 70.1; H, 6.8; N, 8.2%).

The product exhibited hypotensive activity and also anti-convulsant activity.

EXAMPLE 18

4-Benzamido-1-[2-(p-methoxyphenyl)ethyl]piperidine 2-(p-Methoxyphenyl)ethanol p-toluenesulphonate ester (1.53 g.), 4-benamidopiperidine (1.02 g.) and anhydrous potassium carbonate (1.10 g.) were refluxed in isopropanol (50 ml.) for 8 hours and the mixture worked up as in Example 17 to provide the title compound, which was further recrystallised from ethyl acetate as colourless needles (0.78 g.), m.p. 178° C. (Found: C, 74.7; H, 7.9; N, 8.45. $C_{21}H_{26}N_2O_2$ requires C, 74.5; H, 7.7; N, 8.3%).

The product was shown to possess hypotensive activity.

EXAMPLE 19

The following compounds were prepared in a similar manner to that described in the hereinbefore disclosed Examples and processes:

1-(2-Cyclohexylbut-1-yl)-4-benzamidopiperidine.
1-[2-Cyclohexylmethylprop-1-yl]-4-benzamidopiperidine.
1-[4-Cyclohexylbut-2-yl]-4-benzamidopiperidine.
1-[2-(o-Chlorophenyl)ethyl]-4-benzamidopiperidine.
1-[2-(o- and p-Methylphenyl)ethyl]-4-benzamidopiperidine.
1-[2-(o- and p-Ethylphenyl)ethyl]-4-benzamidopiperidine.
1-[2-(o- and p-Propylphenyl)ethyl]-4-benzamidopiperidine.
1-[2-(o- and p-Butylphenyl)ethyl]-4-benzamidopiperidine.
1-(2,6-Dichlorophenylmethyl)-4-benzamidopiperidine.
1-(2,6-Dichlorophenylethyl)-4-benzamidopiperidine.
1-[2-(3,4-Methylenedioxyphenyl)ethyl]-4-benzamidopiperidine.

EXAMPLE 20

| | |
|---|---|
| 1-[2-(3,4-Dimethoxyphenyl)ethyl]-4-benzamidopiperidine | 10 mg. |
| Lactose | 77.5 mg. |
| Dried Maize Starch | 11.75 mg. |
| Magnesium Stearate | 0.75 mg. |

Tablets of the above composition were made by milling the active ingredient to 40 mesh (British Standard), sieving through a 40 mesh (British Standard) sieve, mixing the milled material with the other components, compressing to form tablets, re-granulating, sieving to 20 mesh (British Standard) and then re-compressing to form tablets.

It is understood that any other of the compounds of the invention in the form of the free base or a pharmaceutically acceptable salt or quaternary ammonium salt thereof, may be used in place of the active ingredient of Examples 1, 9, 10, 11, 14, 15, 16, 17 and 18.

The invention includes a method of relieving disorders and diseases of the cardiovascular system especially hypertension in a mammal which comprises administering to said mammal a therapeutically effective amount of a heterocyclic compound of formula formula (Ia)

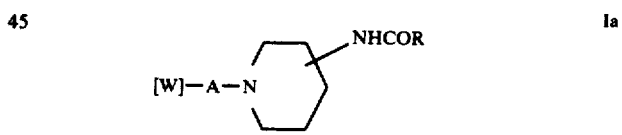

wherein W, A and R are as defined above or a pharmaceutically acceptable acid addition salt thereof.

Tests for action on the cardiovascular system were conducted according to one of the following procedures:

Hypotensive and/or Anti-Hypertensive activity

Method 1 (Rat)

Rats were anaesthetised with pentobarbitone sodium (60 mg/kg) and the jugular vein, trachea and carotid artery were cannulated. The test compound was given intravenously at 15 minute intervals (dose range 0.8–25.6 mg/kg cumulative) and blood pressure and heart rate were recorded via the carotid artery at 30 seconds and 15 minutes after administration. The production of a fall of 30 mm. mercury or more in diastolic pressure from control values was considered to be significant hypotensive activity. A decrease in heart rate of more than 30% from control values was considered to be significant bradycardia.

Method 1 (Cat)

Cats were anaesthetised with pentobarbitone sodium (30 mg/kg) and the cephalic vein, femoral and carotid arteries and trachea were cannulated. The carotid cannula was introduced into the left ventricle and the femoral cannula into the aorta. Blood pressure and heart rate were recorded from the aortic cannula and left ventricular pressure from the carotid cannula. The test compounds were administered intravenously (0.1–25.6 mg/kg).

The following result was obtained with compound 2 above.

Significant lowering of blood pressure (38 mmHg) at 3.2 mg/kg. At this dose myocardial contractile force decreased by 25.7% and heart rate lowered by 28.9% cardiac output was decreased and cardiac effort index was also lowered.

The following result was obtained with compound 4 above.

Significant lowering of blood pressure (52 mmHg) at 3.2 mg/kg. At this dose level myocardial contractile force decreased by 33% and heart rate was lowered by 35%. Cardiac output and cardiac effort index were also lowered.

Method 2 (hypertensive rats)

Male or female rates are rendered hypertensive by applying a figure of 8 ligature around one kidney and contralateral nephrectomy. Blood pressure stablises at a hypertensive level after 6 weeks. Systolic pressure is measured indirectly using a Decker Caudal Plethysmograph. A control group of rats is run with each group treated with drug. Each group usually consists of six rats. Drugs are usually administered by the IP or oral routes. pressures are read prior to drug administration and at two and 24 hours thereafter.

α-Adrenoceptor Antagonism Activity

Carried out on the guinea pig aortic strip [Furchgott and Bhadrakom (1953) J. Pharmac. exp Ther. 108, 129–143]] by the method of Alps et al. [Br. J. Pharmac. 1972, 44, 52–62].

Antihistamine activity as determined by the method of Alps et al. [Br. J. Pharmacol. 1972, 44, 52–62].

Activity in either method 1 (rats or cats) or method 2 was considered to indicate hypotensive activity.

Test results are summarised in the following tables:

Table 1

| Compound of Example | Hypotensive Activity[a] | Anti-hypertensive Activity[b] |
| --- | --- | --- |
| 1 | +++ | +++g |
| 5 | ± | +++ |
| 6 | ++ | +g |
| 7 | + | ± |
| 8 | ± | ± |
| 9 | ++ | ++ |
| 10 | ++ | ++g |
| 11 | ++ | +++ |
| 12 | +++ | + |
| 13 | ± | ± |
| 14 | +++ | +i |
| 15 | ++ | + |
| 16 | + | ++ |
| 17 | ++ | ++ |

Table 1-continued

| Compound of Example | Hypotensive Activity[a] | Anti-hypertensive Activity[b] |
| --- | --- | --- |
| 18 | ++ | ± |

Key: a cumulative iv doses producing a fall in diastolic blood pressure of 30 mm or more, sustained for at least 15 min: 0.8 mg/kg, ++++; 1.6 or 3.2 mg/kg, +++; 6.4 or 12.8 mg/kg, ++; 25.6 mg/kg, +. Falls of <30mm, ±. [b] Falls in systolic blood pressure 2 hr after an oral dose of 40 mg/kg: >50 mm, +++; 50-30 mm, ++30-15 mm, +; <15 mm, ±. g Oral dose of 75 mg/kg. i Oral dose of 2.5 mg/kg.

Table 2

| Example | α-blockade pH$_2$ | Antihistamine pA$_2$ |
| --- | --- | --- |
| 12 | 7.35 | 8.4 |
| 14 | 6.4 | 7.5 |

We claim:

1. A compound of formula Ia

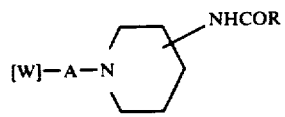

wherein [W] represents cyclohexyl, monohalophenyl, dihalophenyl, lower alkoxyphenyl, dilower alkoxyphenyl, trilower alkoxyphenyl, di(loweralkyl)phenyl, methylenedioxyphenyl, lower alkanoylaminophenyl, nitrophenyl, or aminophenyl. A is lower alkylene of 1 to 6 carbon atoms, and R represents phenyl or a pharmaceutically acceptable acid addition salt thereof.

2. A compound as claimed in claim 1, which is 1-[2-(3,4-dimethoxyphenyl)ethyl]-4-benzamido piperidine or a pharmaceutically acceptable acid addition salt thereof.

3. A compound as claimed in claim 1, which is 1-[2-(3,4-dichlorophenyl)ethyl]-4-benzamidopiperidine or a pharmaceutically acceptable acid addition salt thereof.

4. A compound as claimed in claim 1 which is 1-[2-(cyclohexyl)ethyl]-4-benzamidopiperidine.

5. A compound as claimed in claim 1, which is 1-[2-(p-acetamidophenyl)ethyl]-4-benzamidopiperidine.

6. A compound as claimed in claim 1, which is 1-[2-(o-nitrophenyl)ethyl]-4-benzamidopiperidine or a pharmaceutically acceptable acid addition salt thereof.

7. A compound as claimed in claim 1, which is 1-[2-(o-aminophenyl)ethyl]-4-benzamidopiperidine or a pharmaceutically acceptable acid addition salt thereof.

8. A compound as claimed in claim 1, which is 1-[4-(p-fluorophenyl)-n-butyl]-4-benzamidopiperidine or a pharmaceutically acceptable acid addition salt thereof.

9. A compound as claimed in claim 1, which is 4-benzamido-1-[2-(p-chlorophenyl)ethyl]piperidine.

10. A compound as claimed in claim 1, which is 1-[2-(3,4,5-trimethoxyphenyl) ethyl]-4-benzamidopiperidine or a pharmaceutically acceptable acid addition salt thereof.

11. A compound as claimed in claim 1, which is 1-[2-(3,4-dimethylphenyl)ethyl]-4-benzamidopiperidine or a pharmaceutically acceptable acid addition salt thereof.

12. A compound as claimed in claim 1, which is 4-benzamido 1-(3,4-methylenedioxybenzyl)piperidine or a pharmaceutically acceptable acid addition salt thereof.

13. A compound as claimed in claim 1, which is 4-benzamido-1-[2-(p-methoxyphenyl) ethyl]piperidine or a pharmaceutically acceptable acid addition salt thereof.

* * * * *